US012642587B2

(12) United States Patent
Maier

(10) Patent No.: US 12,642,587 B2
(45) Date of Patent: Jun. 2, 2026

(54) ELECTROSURGICAL SYSTEM AND METHOD FOR DETERMINING AN ELECTRODE TYPE OF A NEUTRAL ELECTRODE

(71) Applicant: Erbe Elektromedizin GmbH, Tuebingen (DE)

(72) Inventor: Philipp Maier, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 417 days.

(21) Appl. No.: 18/136,754

(22) Filed: Apr. 19, 2023

(65) Prior Publication Data
US 2023/0338078 A1 Oct. 26, 2023

(30) Foreign Application Priority Data
Apr. 21, 2022 (EP) ..................................... 22169248

(51) Int. Cl.
*A61B 18/16* (2006.01)
*A61B 18/12* (2006.01)
(Continued)

(52) U.S. Cl.
CPC .......... *A61B 18/16* (2013.01); *A61B 18/1233* (2013.01); *A61B 18/14* (2013.01);
(Continued)

(58) Field of Classification Search
CPC ................ A61B 18/16; A61B 18/1233; A61B 2018/00869; A61B 2018/00875;
(Continued)

(56) References Cited

U.S. PATENT DOCUMENTS 6,007,532 A * 12/1999 Netherly ................ A61N 1/046
606/35
2009/0234352 A1 9/2009 Behnke et al.
(Continued)

FOREIGN PATENT DOCUMENTS

CN 103379873 A 10/2013
CN 101912265 B 10/2014
(Continued)

*Primary Examiner* — Sean W Collins
(74) *Attorney, Agent, or Firm* — Blank Rome LLP

(57) ABSTRACT

Embodiments disclosed include an electrosurgical system as well as a method. The electrosurgical system and the method (are configured to determine an electrode type (T1, T2, T3) of a neutral electrode by applying an alternating measurement signal to the neutral electrode at least at two different measurement frequencies (f1, f2). At each measurement frequency (f1, f2) an impedance absolute value ($ZN_{abs}$) or a phase value ($\varphi$) or both is determined for the neutral electrode impedance (ZN) of neutral electrode. When at least one impedance absolute value ($ZN_{abs}$) and at least one phase value ($\varphi$) is determined, and based on the at least one impedance absolute value ($ZN_{abs}$) and the at least one phase value ($\varphi$), the electrode type (T1, T2, T3) of the connected neutral electrode is determined by comparison with known comparison values for the at least one impedance absolute value ($ZN_{abs}$) and the at least one phase value ($\varphi$).

15 Claims, 5 Drawing Sheets

(51) Int. Cl.
    *A61B 18/14*         (2006.01)
    *A61B 18/00*         (2006.01)

(52) U.S. Cl.
    CPC .............. *A61B 2018/00869* (2013.01); *A61B 2018/00875* (2013.01); *A61B 2018/1253* (2013.01); *A61B 2018/128* (2013.01); *A61B 2018/167* (2013.01)

(58) Field of Classification Search
    CPC ...... A61B 2018/1253; A61B 2018/167; A61B 2018/00648
    See application file for complete search history.

(56)               References Cited

U.S. PATENT DOCUMENTS

| | | | |
|---|---|---|---|
| 2010/0331835 A1 | 12/2010 | Shilev | |
| 2011/0202055 A1 | 8/2011 | Selig | |
| 2012/0232548 A1* | 9/2012 | Behnke, II | ......... A61B 18/1233 |
| | | | 606/35 |
| 2012/0323236 A1* | 12/2012 | Hagg | ................. A61B 18/1233 |
| | | | 606/41 |
| 2020/0100825 A1* | 4/2020 | Henderson | ......... H04L 63/0245 |
| 2020/0121381 A1 | 4/2020 | Fähsing | |

FOREIGN PATENT DOCUMENTS

| | | |
|---|---|---|
| DE | 10 2019 209 333 A1 | 12/2020 |
| EP | 0 813 387 A1 | 12/1997 |
| EP | 1 289 415 A1 | 3/2003 |
| EP | 2 537 479 A1 | 12/2012 |
| EP | 2620113 A1 | 7/2013 |
| EP | 3 496 638 A1 | 6/2019 |
| RU | 2014145823 A | 6/2016 |
| WO | 9627327 A1 | 9/1996 |
| WO | 0187154 A1 | 11/2001 |
| WO | 03060462 A2 | 7/2003 |
| WO | 2013158537 A2 | 10/2013 |
| WO | 2018029154 A1 | 2/2018 |
| WO | 2019238352 A1 | 12/2019 |

* cited by examiner

ELECTROSURGICAL SYSTEM AND METHOD FOR DETERMINING AN ELECTRODE TYPE OF A NEUTRAL ELECTRODE

CROSS-REFERENCE TO RELATED APPLICATION

This application claims priority to European Patent Application No. 22169248.6, filed Apr. 21, 2022, the entirety of which is incorporated by reference herein.

TECHNICAL FIELD

The invention refers to an electrosurgical system as well as a method for determining an electrode type of a neutral electrode. The electrosurgical system is particularly a system having a monopolar instrument and a neutral electrode that can be connected or are connected to a supply apparatus of the electrosurgical system. The neutral electrode is configured to be attached to a patient in an electrically conductive manner, e.g., by an adhesive connection. The method can be carried out using the electrosurgical system according to the invention. The electrosurgical system can be particularly configured for carrying out the method according to the invention.

BACKGROUND

In the electrosurgical system during treatment of a patient the current circuit from the supply apparatus to the working electrode of the instrument and back to the supply apparatus has to be closed. For this purpose, in a monopolar instrument, an additional electrode, which can be denoted as neutral electrode, can be attached to the patient. The current can thus flow from the supply apparatus to the working electrode, from the working electrode into the patient, through the tissue of the patient to the neutral electrode and from there back to the supply apparatus.

In electrosurgical systems with monopolar instruments, different kinds of electrodes or electrode types of neutral electrodes can be used. The different electrode types of neutral electrodes can comprise surface areas of the at least one electrically conductive electrode section (contact area) of different size that is in contact with the patient. The at least one electrically conductive electrode section of the neutral electrode can also have different geometries or dimensions in a longitudinal direction and/or a transverse direction for different electrode types.

The current density at the neutral electrode must not become too high so as to avoid endogenous burns during operation of the electrosurgical system.

EP 2 537 479 A1 describes the control of a medical apparatus dependent on the neutral electrode impedance. The impedance is compared with a predefined threshold and the operation of the electrosurgical system or the treatment instrument is only allowed, if the impedance of the neutral electrode is within a predefined range, e.g. at most 140 Ohm. In doing so, it can be tested whether the neutral electrode is correctly attached to the patient and whether a sufficiently good electrical connection to the patient exists.

The measurement of impedances of biological tissue is known in the field of impedance spectroscopy. In the impedance spectroscopy tissue types shall be distinguished that are treated by means of the electrosurgical instrument of the electrosurgical system. For example, EP 1 289 415 A1 describes such a method. By means of the instrument a test signal is applied to the treated tissue at different frequencies and based on the measured impedance, the tissue is characterized. In this manner the distinction of different tissue types is possible. A similar method is also described in EP 0 813 387 A1.

In the method known from WO 03/060462 A2 an electrical pulse is supplied into the tissue of a patient and the reflection of the supplied pulse is detected. Based on the reflection, healthy tissue shall be distinguished from malign tissue in real time.

An electrosurgical system having a measurement unit is described in EP 3 496 638 A1. There an impedance measurement of the treated tissue is carried out at different frequencies by means of the measurement device. A measurement signal can be applied to the tissue by means of the measurement device. A switching device serves to switch between a voltage for treatment of the tissue and the measurement signal. By means of the measurement signal the impedance of the tissue is determined at different frequencies.

A method for determination of a local tissue type of body tissue and respective electrosurgical system are described in DE 10 2019 209 333 A1. For tissue determination a measurement signal (alternating voltage or alternating current) are coupled into the tissue. The frequency of the measurement signal may vary. Based thereon an impedance spectrum can be determined and therefrom the tissue type can be derived in turn.

SUMMARY

Embodiments disclosed herein include an electrosurgical system and a method that improves the use of a neutral electrode and particularly increases the safety when using the neutral electrode.

Embodiments include an electrosurgical system having the features functionality of the claims.

An electrosurgical system described herein comprises a supply apparatus, having a neutral connection, and a neutral electrode connected to the supply apparatus' neutral connection. The neutral electrode is configured to be connected to the patient in an electrically conductive manner. As an example, the neutral electrode can be adhesively connected to the skin of the patient or can be attached.

The supply apparatus can be configured to apply an alternating measurement signal at least at two different measurement frequencies to the neutral connection. The measurement signal can be an alternating voltage measurement signal or an alternating current measurement signal. For example, the measurement signal can have a sinusoidal or co-sinusoidal shape, a triangular shape, a saw tooth shape or a square wave shape.

If the measurement signal is an impressed alternating measurement voltage, an alternating measurement current flowing through the neutral electrode or an electrode current circuit is produced thereby. If the measurement signal is an impressed alternating measurement current, an alternating measurement voltage at the neutral electrode or at the electrode current circuit is produced thereby. The electrode current circuit comprises a closed current circuit from the supply apparatus through the tissue of the patient to the neutral electrode and back to the supply apparatus. The supply apparatus includes an instrument. Preferably the instrument is not part of the electrode current circuit and the electrode current circuit is closed by two separate electrically conductive electrode sections of the neutral electrode that are connected to the supply apparatus as well as to the patient in an electrically conductive manner in each case. In doing so, the electrode current circuit can lead from a neutral connection of the supply apparatus to a first electrode section, via the tissue of the patient to a second electrode section and back to the neutral connection of the supply apparatus.

The alternating measurement signal can be a measurement signal that varies periodically. The measurement signal can change its polarity and thus the current flow direction alternatingly. Alternatively, to this the measurement signal could also be positive or always negative.

Thus, the measurement signal creates an alternating measurement current and an alternating measurement voltage at the neutral electrode or at the neutral connection of the supply apparatus from an impedance absolute value of a neutral electrode impedance of the neutral electrode (apparent impedance) and a phase value of the neutral electrode impedance can be determined. The impedance absolute value is determined at least for one of the measurement frequencies and the phase value is determined at least for one of the measurement frequencies. At each of the used measurement frequencies the impedance absolute value and/ or the phase value is determined.

Based on the at least one impedance absolute value and the at least one phase value the electrode type of the connected neutral electrode can be determined or recognized. For this purpose comparison values for the phase value and the impedance absolute value at the used measurement frequencies can be stored (e.g. in the form of a table or in the form of one or more comparison curves), so that the electrode type of the neutral electrode can be recognized a comparison.

Due to the recognition of the electrode type, the supply apparatus can be switched automatically or manually into an operating mode, which is adapted to the electrode type of the neutral electrode. If multiple operating types are possible, they can be provided to the user for selection and/or a standard mode can be automatically selected therefrom. By the at least one operating mode, which is adapted to the electrode type, the electrical power or the working current can be adjusted and/or limited, for example. The current density in the tissue of the patient below the neutral electrode is dependent on the electrode type, particularly on the total area content of the at least one electrically conductive electrode section. Thus, the current density can be limited in a manner, which is adapted to the size and/or geometry of the electrode type. For example, depending on the determined electrode type, a limit value for the electrical power and/or the current flowing through the neutral electrode can be used.

The determination of the electrode type allows, additionally or alternatively to the determination or limitation of the current density, the determination of at least one additional parameter that can be used during operation of the supply apparatus. For example, the at least one additional parameter can be selected from the following group: a temperature of the patient's tissue in the area in which the neutral electrode is attached; an area content of the effective contact area between the neutral electrode and the patient; the presence of a contact gel between the neutral electrode and the patient.

It is advantageous, if the supply apparatus is configured to determine at least one phase value at a different measurement frequency than the at least one impedance absolute value.

It is advantageous, if the supply apparatus is configured to determine an impedance absolute value for a first measurement frequency and a phase value of the neutral electrode impedance for a second measurement frequency. The second measurement frequency is lower than the first measurement frequency. The first measurement frequency is preferably selected from a range of 5.0 kHz to 1.0 MHz. The second measurement frequency can be selected from a range of 100 Hz to 5.0 kHz. Optionally also an impedance absolute value can be determined at the second measurement frequency and/or in addition a phase value can be determined at the first measurement frequency. Alternatively it is also possible to determine an impedance absolute value at the first measurement frequency exclusively and to determine a phase value at the second measurement frequency exclusively.

The amplitude of the measurement signal can be limited, particularly during measurement for determination of a phase value and/or during measurement with one of the measurement frequencies, e.g. the second measurement frequency. The amplitude of the alternating measurement voltage is preferably lower than 5 V. The amplitude of an alternating current measurement signal is particularly smaller than 1.0 mA.

The electrosurgical system can comprise a multiplicity of neutral electrodes of different electrode types from which a neutral electrode of one electrode type can be selected and connected to the supply apparatus. Each electrode type can comprise multiple, e.g. two or three, separate electrode sections. The electrode sections are not short-circuited in the neutral electrode. They may have different electrical potentials. Within the neutral electrode the electrode sections are preferably electrically insulated from one another for the occurring electrical currents and voltages. An electrical connection between two electrode sections exists, particularly only indirectly via the tissue of the patient, if the neutral electrode is attached to the patient.

The electrode types can distinguish from one another by one or more type parameters, for example:

- the number of present electrically conductive electrode sections;
- the total area content of all present electrically conductive electrode sections;
- the contour or geometry of the at least one electrically conductive electrode section;
- the electrically conductive material used for the at least one electrode section;
- the relative position of two or more provided electrode sections relative to each other.

For example, at least one electrode type of the neutral electrode comprises exactly two electrically conductive electrode sections. Another electrode type of the neutral electrode comprises exactly three electrically conductive electrode sections.

Preferably at least two of the present electrode sections are connected or can be connected with the neutral connection of the supply apparatus by one conductor in each case. For example, a first electrode section can be electrically connected via a first conductor and a second electrode section can be electrically connected via a second conductor with the neutral connection of the supply apparatus. The two conductors are electrically insulated from one another for the occurring currents and voltages.

At least in one of the electrode types or in all of the electrode types a first electrode section and a second electrode section can be arranged symmetrically to a reference plane.

In an embodiment the first electrode section and the second electrode section can have equal area contents and/or an identical geometry.

The first electrode section and the second electrode section can be arranged with distance to one another and can be separated by an electrically non-conductive web of the neutral electrode, for example.

At least in one of the electrode types the neutral electrode has an electrically conductive third electrode section. The third electrode section is electrically insulated from all other electrode sections within the neutral electrode, e.g. from the first electrode section and the second electrode section, for the occurring currents and voltages.

In at least one electrode type the third electrode section can surround the first electrode section and the second electrode section. In its extension direction the third electrode section is preferably curved and/or bent in multiple portions. It is preferred, if the third electrode section is realized without interruption in its extension direction between its two ends. For example, the third electrode section can have a progress that is open at one single opening site, whereby the two ends are arranged opposite one another at the opening site. For example, the third electrode section can be U-shaped or C-shaped. At the opening site of the third electrode section a connection area can be provided for the electrode sections that are surrounded by the third electrode section, e.g. a connection area for the first conductor to the first electrode section and for the second conductor to the second electrode section.

The area content of the third electrode section can be smaller than the area content of any other provided electrode section, particularly of the first electrode section and the second electrode section. The length of the third electrode section in its extension direction between the two ends can be preferably larger about the multiplier 10 or 20 than the magnitude of its maximum width orthogonal to this extension direction (length).

Different electrode types can also distinguish in a manner from one another, how the outer edge of the first electrode section and the second electrode section is realized, wherein the outer edge is present at the outer sides of the electrode sections facing away from one another. In one electrode type these outer edges can be curved in an arc-shaped manner and/or can have no straight section and/or can have no section extending parallel to the reference plane, wherein the reference plane extends centrally between the two electrode sections and can form a symmetry plane. In another electrode type the outer edges can have a straight section and/or a section extending parallel to the reference plane.

It is advantageous, if the supply apparatus comprises a supply connection and an instrument that is connected or can be connected to the supply connection. The instrument connected to the supply connection is supplied with a working signal by the supply apparatus and thus an electrical working power, wherein a working voltage or a working current can be impressed as working signal. The instrument has a working electrode to which the working signal is supplied. During the use of the electrosurgical system tissue of the patient can be coagulated, cut, ablated or fusioned by the instrument. Depending on the function, the working signal (working voltage and/or working current) can vary, e.g. with regard to the working frequency, the amplitude, the wave form or an arbitrary combination thereof.

The supply apparatus can be configured to apply the measurement signal to the neutral connection only, if the working electrode is not supplied with working voltage and/or working current. Thus, a measurement signal is only applied to the neutral electrode, if no current flows back via the neutral electrode that has been supplied into the patient's tissue by the working electrode. In doing so, the determination of the impedance absolute value and the phase value is not affected by a working current that produces a current flow through the neutral electrode.

Additionally or alternatively, it is also possible to concurrently treat tissue by the working electrode (a voltage is applied to the working electrode and/or a current flows through the working electrode) and to apply the measurement signal to the neutral connection, at least in phases. In the phases or periods in which a treatment period and the application of the measurement signal overlaps, the measurement frequency of the measurement signal can be different from the frequency of the working signal (working voltage and/or working current). In doing so, it is guaranteed that the measurement current produced by the alternating voltage measurement signal or the measurement voltage produced by the alternating current measurement signal can be distinguished from the working voltage and/or the working current flowing back through the neutral electrode—for example by evaluation of the frequency. Therefore, also in this case a sufficiently precise determination of the at least one impedance absolute value and/or the at least one phase value is possible.

The method according to the invention can be carried out by using any embodiment of the electrosurgical system, as described above for example. First, the neutral electrode of a selected electrode type is attached to the patient so that an electrically conductive connection exists between the neutral electrode and the patient. Subsequently, an alternating measurement signal is applied to the neutral electrode, particularly via the electrical connection of the neutral electrode with the neutral connection of a supply apparatus. The measurement signal is applied at least at two different measurement frequencies. Based on the measurement signal, at least one impedance absolute value (apparent impedance) of a neutral electrode impedance of the neutral electrode is determined at least at one of the measurement frequencies. In addition, a phase value of the neutral electrode impedance is determined at least at one of the measurement frequencies. For each measurement frequency an impedance absolute value and/or a phase value is determined.

Subsequently, the electrode type of the connected neutral electrode can be determined based on the at least one impedance absolute value and the at least one phase value.

BRIEF DESCRIPTION OF THE DRAWINGS

Advantageous embodiments in accordance with the invention are derived from the claims, the drawing and the description. In the following, preferred embodiments in accordance with the invention are described in detail with reference to the attached drawing. The drawing shows:

DETAILED DESCRIPTION

Figure 1:
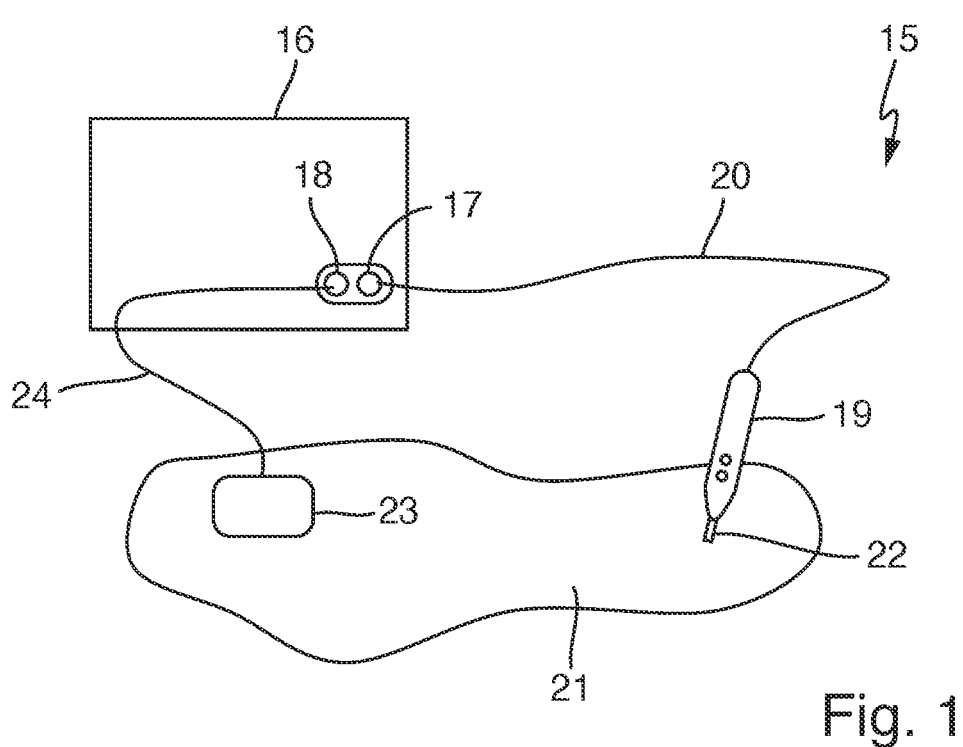
FIG. 1 a schematic block-diagram-like illustration of an embodiment of an electrosurgical system comprising a supply apparatus, a neutral electrode and an instrument, FIG. 2 a block diagram of an embodiment of an electrosurgical system, FIG. 3 a flow diagram of an embodiment of a method according in accordance with the invention, FIG. 4 a schematic basic illustration of an embodiment of a first electrode type of a neutral electrode, FIG. 5 a schematic basic illustration of an embodiment of a second electrode type of a neutral electrode, FIG. 6 a schematic basic illustration of an embodiment of a third electrode type of a neutral electrode, FIG. 7 a schematic exemplary illustration of impedance absolute values of the electrode types according to FIGS. 4 to 6 depending on a measurement frequency, FIG. 8 schematic exemplary illustrations of phase values for the electrode types according to FIGS. 4 to 6 depending on the measurement frequency, FIGS. 9 to 11 an exemplary time-dependent progress of a working signal (working voltage and/or working current) at a working electrode of the instrument as well as a measurement signal (alternating voltage measurement signal and/or alternating current measurement signal) at a neutral electrode respectively.

In FIG. 1 a basic illustration of an embodiment of an electrosurgical system 15 is illustrated. The electrosurgical system 15 has a supply apparatus 16 comprising a supply connection 17 as well as a neutral connection 18. The supply connection 17 serves to electrically connect an instrument 19 with a supply apparatus 16. The electrical connection can be a single pole or multi-pole connection. The connection can be established by a single core or multi-core cable 20.

The instrument 19 is configured for electrosurgical treatment of biological tissue 21 of a patient. The tissue 21 is biological tissue of a human or animal body. For treatment of tissue 21, the instrument 19 comprises at least one or exactly one working electrode 22. For treatment of tissue 21, an electrically conductive connection between the working electrode 22 and the tissue 21 can be established.

In the electrosurgical system 15 illustrated in FIG. 1 instrument 19 is a monopolar instrument. A current circuit between the supply apparatus 16, the working electrode 22 of instrument 19 and back to the supply apparatus 16 is not exclusively established by instrument 19, but in addition by a separate electrode that is electrically conductively attached to the patient. This additional electrode is denoted as neutral electrode 23. The neutral electrode 23 is electrically connected with the neutral connection 18 of supply apparatus 16, according to the example by a multi-core cable 24. The cable 24 has two cores or conductors that are denoted as first conductor 25 and second conductor 26 in the described embodiment (FIGS. 2 and 4 to 6).

Figure 2:
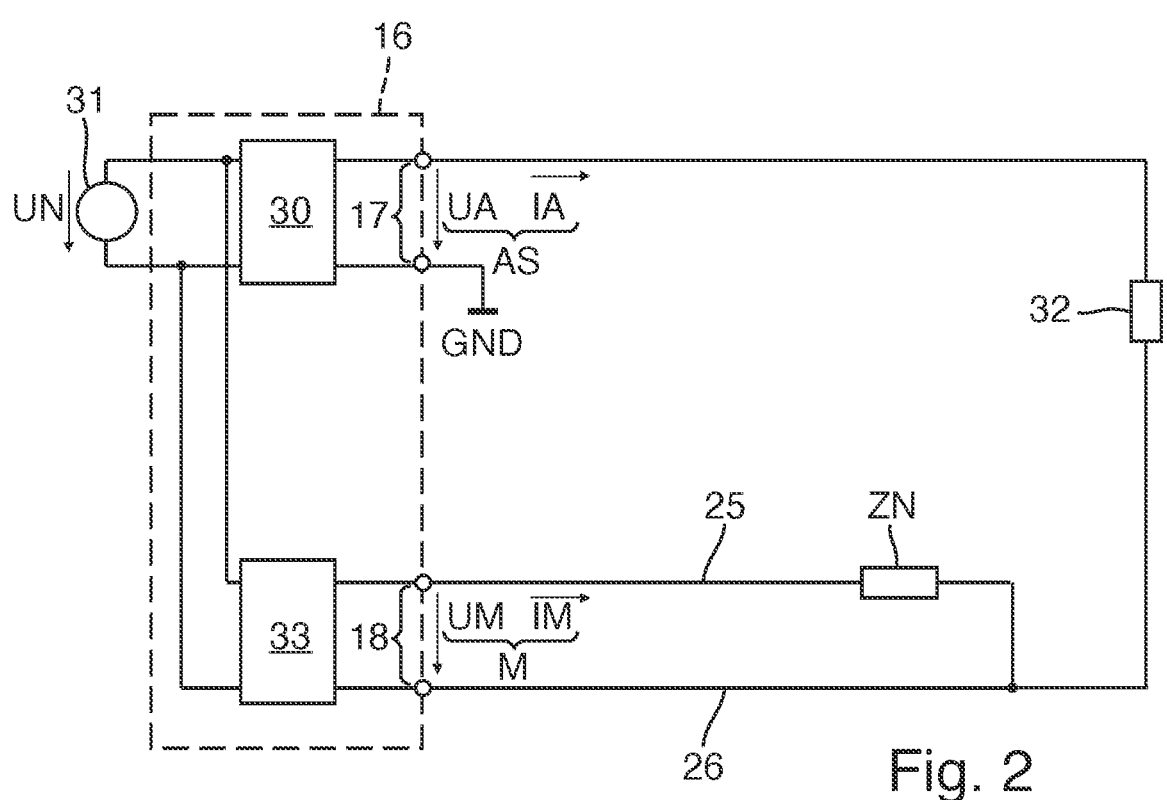

In FIG. 2 a block diagram of the electrosurgical system 15 according to FIG. 1 is illustrated. In the embodiment, the supply apparatus 16 comprises an inverter circuit 30 that is connected to an external energy supply, e.g., a grid voltage source 31 of an energy supply grid. The grid voltage source 31 provides a grid voltage to the supply apparatus 16 and according to the example the inverter circuit 30. The inverter circuit 30 is configured to provide or impress a working signal AS to or at the supply connection 17. The working signal AS provided at the supply connection 17 by supply apparatus 16 can be an impressed working voltage UA or an impressed working current IA, wherein the working voltage UA can produce a working current IA or the working current IA can produce a working voltage UA at the supply connection 17. The working signal AS is a high frequency signal, i.e., the working voltage UA is a high frequency voltage and/or the working current IA is a high frequency current. The working signal AS is supplied to the working electrode 22 during treatment of tissue 21. During treatment, the working current IA flows via the working electrode 22 into the tissue 21 to the neutral electrode 23 and to the supply apparatus by the neutral connection 18. The total impedance of this working current circuit can be denoted as working impedance 32.

In the illustrated embodiment, the working signal AS is requested at the supply connection 17 by the instrument 19 (FIG. 1) via a signal line of cable 20 (FIG. 1). During one or multiple treatment periods P (FIGS. 9-11), working signal AS at the supply connection 17 is then applied to working electrode 22 of the instrument.

As an option, the working signal AS can also be continuously provided for the instrument 19 at supply connection 17. In this case, instrument 19 can have a switching device in order to provide a suitable voltage and/or a suitable current to the working electrode 22 during treatment periods P (FIGS. 9-11) based on the working signal AS. The switching device can optionally comprise an inverter circuit or another modification circuit in order to convert or modify the working signal AS, if necessary.

Also, a combination of these described embodiments for providing suitable electrical power to the working electrode 22 is possible.

The working voltage UA corresponds to a potential difference between a working potential and a reference potential, e.g., ground GND.

In the illustrated embodiment, supply apparatus 16 comprises in addition a measurement unit 33. The measurement unit 33 is configured to provide or impress an alternating measurement signal M at the neutral connection 18. The measurement signal M can be an alternating measurement voltage UM or an alternating measurement current IM. The waveform of the alternating measurement signal M and/or the amplitude of the measurement signal M can vary. For example, measurement signal M can be sinusoidal-shaped or co-sinusoidal-shaped, triangular-shaped or square-wave-shaped. The measurement frequency f has a magnitude of preferably at least 100 Hz and at most 1 MHz.

Depending on whether the alternating measurement voltage UM or the alternating measurement current IM is impressed, the measurement signal M produces an alternating measurement current IM through the electrode current circuit or an alternating measurement voltage UM at the electrode current circuit. The electrode current circuit leads from the first conductor 25 via the neutral electrode 23, tissue 21 of the patient and again via neutral electrode 23 and the second conductor 26 back. The neutral electrode impedance ZN in the electrode current circuit is characterized by an impedance absolute value $ZN_{abs}$ as well as a phase value φ. For the neutral electrode impedance ZN applies:

$$ZN = ZN_{abs} \cdot e^{j\varphi} \tag{1}$$

$$ZN = \mathrm{Re}(ZN) + j \cdot \mathrm{Im}(ZN) \tag{2}$$

$$ZN_{abs} = \sqrt{\mathrm{Re}(ZN)^2 + \mathrm{Im}(ZN)^2} \tag{3}$$

$$\varphi = \arctan 2(\mathrm{Im}(Zn), \mathrm{Re}(Zn)) \tag{4}$$

Re(ZN) is thereby the true neutral electrode impedance ZN and Im(ZN) is the calculated neutral electrode impedance ZN. The calculated Im(ZN) and the true Re(Zn) can depend on a measurement frequency f of the alternating measurement signal M.

The measurement unit 33 is configured to determine an impedance absolute value $ZN_{abs}$ and/or a phase value φ based on the alternating measurement voltage UM and the alternating measurement current IM for two or more measurement frequencies f respectively. The phase shift between alternating measurement voltage UM and alternating measurement current IM results from capacitive effects in the electrode current circuit according to the example, particularly from capacitive effects between neutral electrode 23 and tissue 21 of the patient. These capacitive effects are characterized by the neutral electrode impedance ZN. The neutral electrode impedance ZN also describes ohmic resistances and as an option also inductive effects in the electrode current circuit. The impedance absolute value $ZN_{abs}$ can be denoted as apparent impedance.

Figure 6:
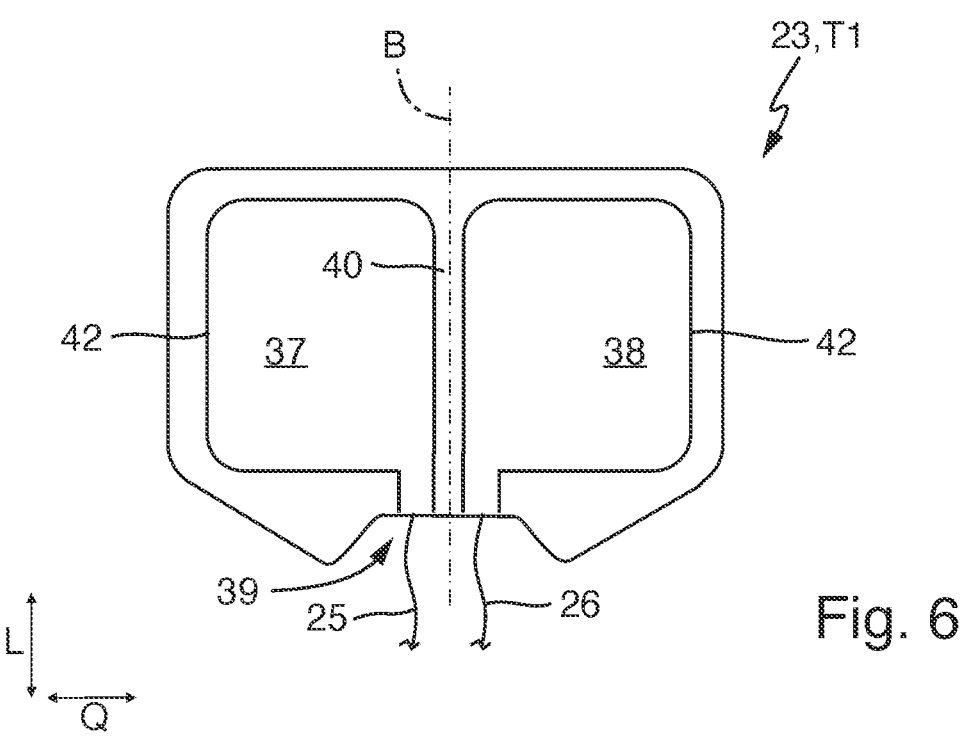

Different electrode types of neutral electrodes 23 are provided for the electrosurgical system 15. Only by way of example, three different electrode types are illustrated here, namely a first electrode type T1 (FIG. 4), a second electrode type T2 (FIG. 5) as well as a third electrode type T3 (FIG. 6).

The two-dimensional neutral electrode 23 extends in a non-deformed initial condition substantially parallel to a plane that is spanned by a longitudinal direction L and the transverse direction Q. The description of the geometric characteristics of neutral electrode 23 refer to this initial condition.

In the embodiment each of the electrode types T1, T2, T3 have at least two electrically conductive electrode sections, namely an electrically conductive first electrode section 37 as well as an electrically conductive second electrode section 38. In a connection area 39 of neutral electrode 23 the first electrode section 37 is electrically connected with first conductor 25 and second electrode section 38 is electrically connected with second conductor 26. In the connection area 39 the first electrode section 37 as well as the second electrode section 38 each have a strip conductor-like extension or a strip conductor-like prolongation to which the assigned conductor 25 or 26 is connected. This extension extends in longitudinal direction L of neutral electrode 23 in the embodiments illustrated here.

The first electrode section 37 and the second electrode section 38 of each electrode type T1, T2, T3 are identically dimensioned in the embodiment and thus have equal area contents and the same geometry. Relative to a reference plane B, first electrode section 37 and second electrode section 38 are arranged symmetrically and are electrically and spatially separated from one another by a web 40 located in between. The reference plane B extends parallel to the longitudinal direction L and is orientated orthogonal to a transverse direction Q.

The first electrode type T1 distinguishes from a second electrode type T2 and electrode type T3, in that in addition to the first electrode section 37 and the second electrode section 38 an electrically conductive third electrode section 41 is present. The neutral electrode 23 of first electrode type T1 has exactly three electrode sections 37, 38, 41 according to the example, whereas the neutral electrode 23 of second electrode type T2 and third electrode type T3 only have two electrode sections 37, 38.

The third electrode section 41 of neutral electrode 23 of first electrode type T1 is not electrically connected or connectable to supply apparatus 16 different to the other electrode sections 37, 38. Its electrical potential thus cannot directly be set by supply apparatus 16.

All of the electrode sections 37, 38, 41 of all electrode types T1, T2, T3 of neutral electrodes 23 are not directly electrically connected with one another within the neutral electrode 23, but are electrically insulated from one another with regard to the voltages and currents occurring in the error-free normal operation. An electrical connection is indirectly established in the operation position via the tissue 21 of the patient. The neutral electrodes 23 are provided with the electrically conductive electrode sections 37, 38, 41 on the side that is attached to the tissue 21 of the patient in the operation position. The opposite back side facing away from tissue 21 is preferably electrically insulated so that a protection against contact is provided for the treating personnel. For example, the electrode sections 37, 38, 41 can be applied on a substrate material of neutral electrode 23 and can be covered and thereby electrically insulated on the back side by the substrate material or a cover layer.

Figure 4:
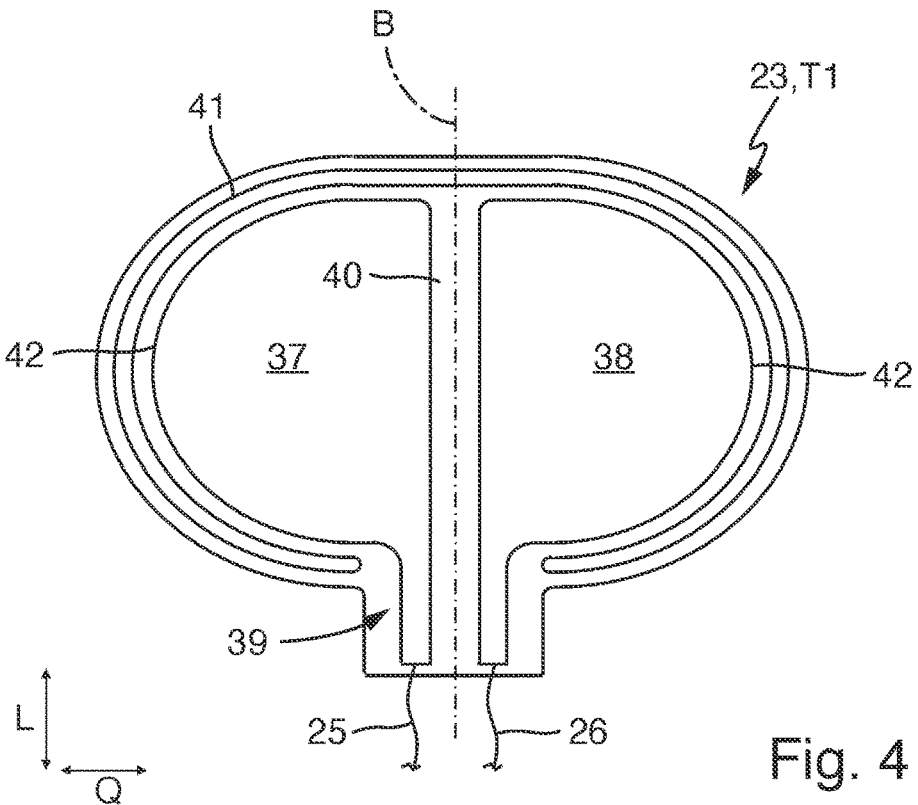
Figure 5:
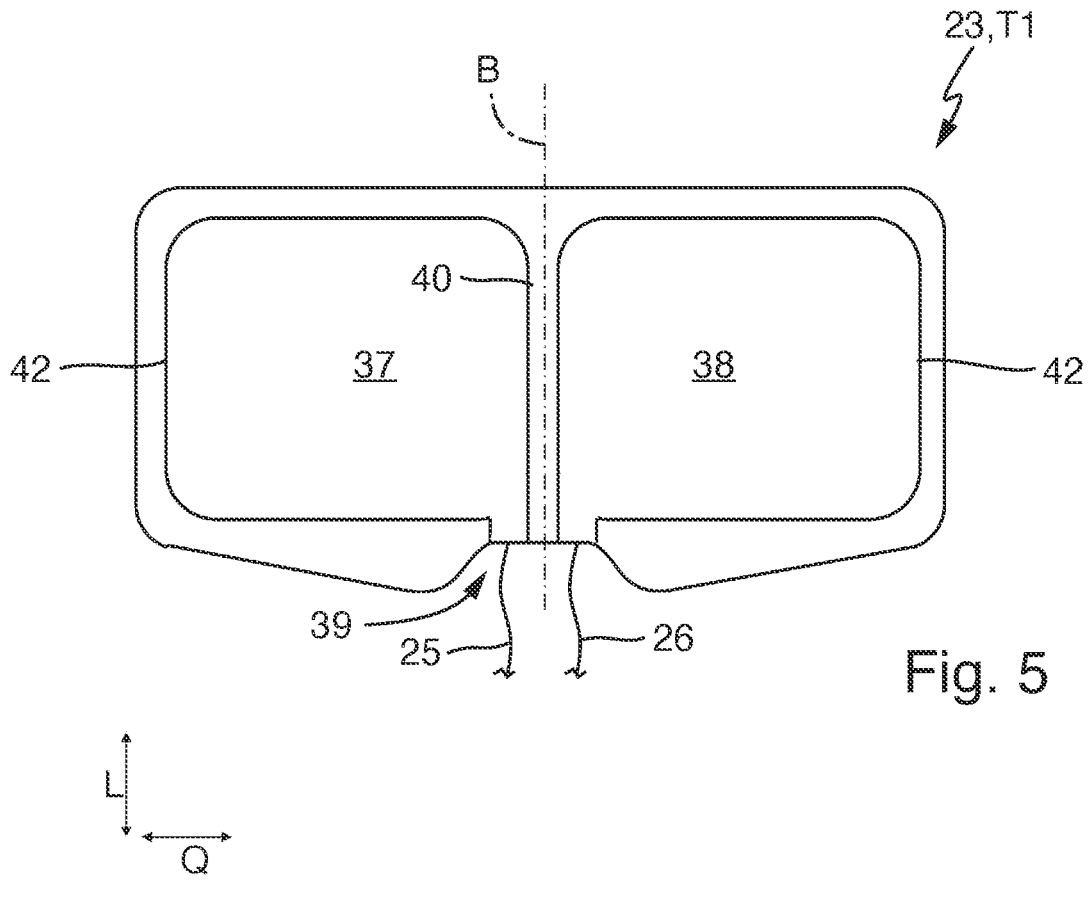

As schematically illustrated in FIG. 4, third electrode section 41 remarkably distinguishes from the geometry of the other electrode sections 37, 38. According to the example, it extends around the first electrode section 37 and the second electrode section 38, whereby it is particularly exclusively open in the connection area 39. The two ends of the third electrode section 41 are arranged with distance opposite one another in transverse direction Q. Between these two ends the third electrode section 41 extends without interruption around the first electrode section 37 and the second electrode section 38. The length of the third electrode section 41 in its extension direction between its two ends is at least about the multiplier 10 or the multiplier 20 larger than its width orthogonal to this extension direction. Thereby third electrode section 41 has a line-shaped form.

The number of electrically conductive electrode sections 37, 38, 41 is thus a distinction criterion for distinguishing different electrode types T1, T2, T3. Additionally or alternatively, electrode types T1, T2, T3 can be distinguished from one another by one or multiple of the following distinguishing features:

the area content of one, multiple or all present electrode sections 37, 38, 41;

the contour or geometry of one, multiple or all present electrode sections 37, 38, 41;

the electrically conductive material that is used for the electrode sections 37, 38, 41;

the relative position of the present electrode sections 37, 38, 41 relative to one another.

It is apparent in the illustrated embodiments that the first electrode type T1 also distinguishes from second electrode type T2 and third electrode type T3 in that first electrode section 37 and second electrode section 38 have different geometries. In the first electrode type T1 first electrode section 37 and second electrode section 38 have an outer edge 42 on the outer sides facing away from one another extending in an arc-shaped and according to the example circular arc-shaped manner. On the contrary, the outer edges 42 are at least in sections straight and extend in the embodiment in longitudinal direction L in the second electrode type T2 and in the third electrode type T3.

In the first electrode type T1 of neutral electrode 23 the first electrode section 37 and the second electrode section 38, therefore, have substantially the shape of a semi-circle or a semi-oval respectively and in the second electrode type T2 and the third electrode type T3 substantially the shape of a square or rectangle with rounded edges respectively.

The second electrode type T2 and the third electrode type T3 mainly distinguish by the dimension of the electrode sections 37, 38. In the second electrode type T2 a width of the electrode sections 37, 38 in transverse direction Q is at least as large as a length of the electrode sections 37, 38 in longitudinal direction L. On the contrary, in the third electrode type T3 the length of the electrode sections 37, 38 in longitudinal direction L is larger than the width of the electrode sections 37, 38 in transverse direction Q.

The electrode types T1, T2, T3 illustrated here are only examples for possible different electrode types. Additionally or alternatively, one or multiple additional electrode types can be present. For example, electrode types can be used in which the first electrode section 37 and the second electrode section 38 distinguish by geometry from the electrode types T1, T2, T3 illustrated here and comprise, for example, other polygonal shapes with or without rounded edges.

Figure 3:
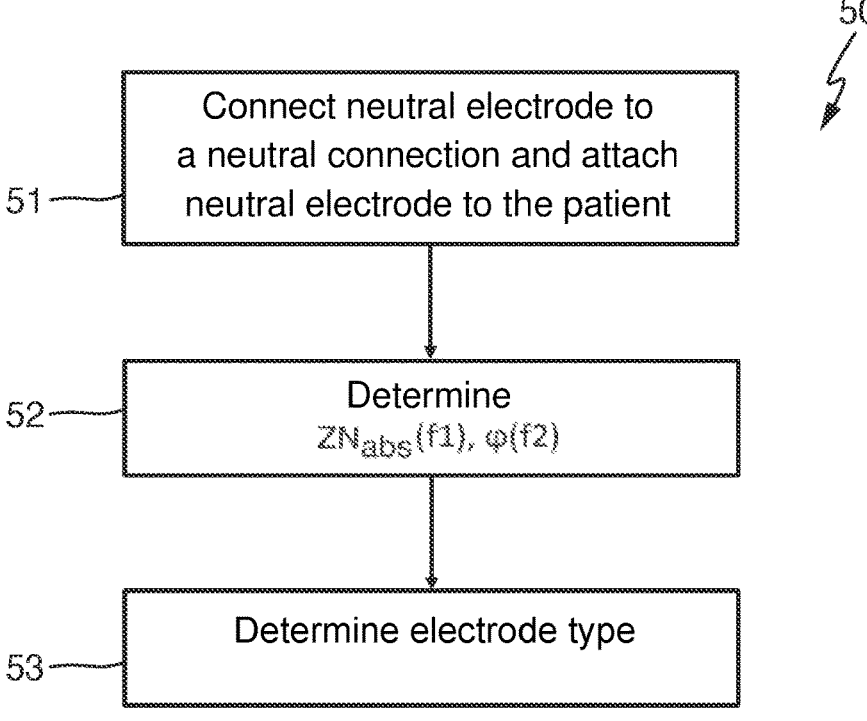

The electrode types T1, T2, T3 connected to the neutral connection 18 is automatically determined as illustrated in the flow diagram of FIG. 3. In step 51, neutral electrode 23 of the respective electrode type T1, T2, T3 is connected to neutral connection 18 of supply apparatus 16 and attached to the patient so that the provided electrode sections 37, 38 and optionally 41 are in electrically conductive contact with the patient (particularly the skin of the patient). The neutral electrode 23 can be self-adhesive, for example.

In step 52, at least one impedance absolute value $ZN_{abs}$ and at least one phase value $\varphi$ is determined by measurement unit 33. For example, it can be sufficient to determine one impedance absolute value $ZN_{abs}$ for a first measurement frequency f1 and one phase value $\varphi$ for a second measurement frequency f2, wherein the second measurement frequency f2 is lower than the first measurement frequency f1. The first measurement frequency f1 and the second measurement frequency f2 are preferably selected from a frequency range of 100 Hz to 1.0 MHz. The first measurement frequency f1 can have a magnitude of minimum 5.0 kHz, e.g. 14 kHz to 15 kHz. According to the example, the second measurement frequency f2 has a magnitude of maximum 5.0 kHz, preferably maximum 1.0 kHz. In the embodiment the second measurement frequency f2 is selected close to the lower range limit of the frequency range and can be equal to 100 Hz, for example, or can be in the range of 100 Hz to 200 Hz.

Based on the at least one impedance absolute value $ZN_{abs}$ and the at least one phase value $\varphi$ in a third method step 53, electrode type T1, T2, T3 of the connected neutral electrode 23 can be determined.

Due to the recognition of the electrode type T1, T2, T3 of the connected neutral electrode 23, supply apparatus 16 can preset at least one operating mode adapted to the electrode type T1, T2, T3. The operating mode or one of the possible operating modes can be set automatically or can be selected manually by the user. For example, depending on the determined electrode type T1, T2, T3, a limit value for the electric power and/or the current flowing through the neutral electrode 23 can be used. The current density in the tissue 21 can thus be limited in a manner adapted to the size and/or geometry of the electrode type T1, T2, T3.

The determination of the at least one impedance absolute value $ZN_{abs}$ and the at least one phase value $\varphi$ at one assigned measurement frequency f1, f2 respectively is sufficient. At the first measurement frequency f1 and at the second measurement frequency f2 one impedance absolute value $ZN_{abs}$ and/or one phase value $\varphi$ is determined respectively. In modification to the embodiment illustrated here, also more than two measurement frequencies f1, f2 can be used for determination of the at least one impedance absolute value $ZN_{abs}$ and the at least one phase value $\varphi$. The number of the determined impedance absolute values $ZN_{abs}$ and the number of determined phase values $\varphi$ can be equal or of different amount. If two or more impedance absolute values $ZN_{abs}$ and/or two or more phase values $\varphi$ are determined, the two or more impedance absolute values are determined at different measurement frequencies f and/or the two or more phase values $\varphi$ are determined at different measurement frequencies f1, f2.

Figure 9:
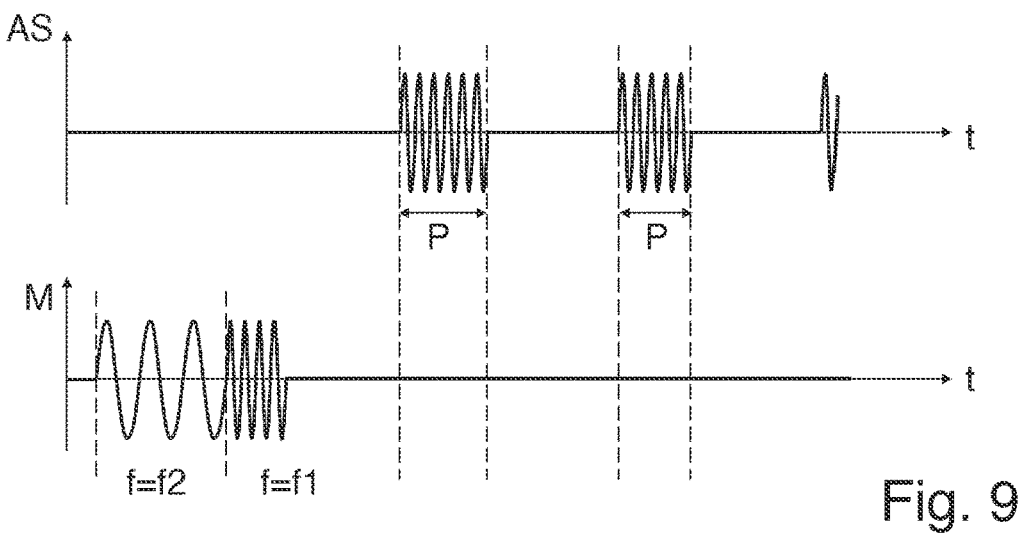
Figure 10:
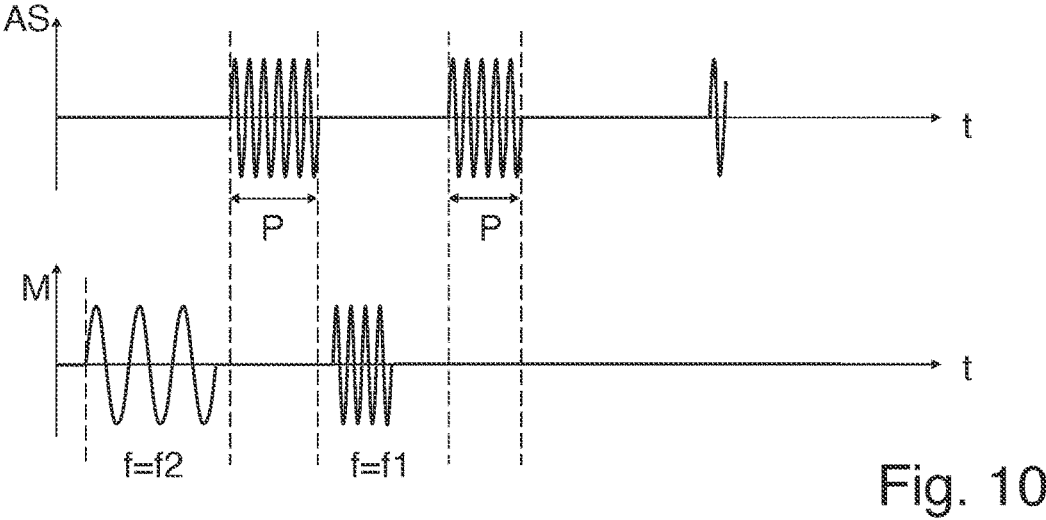
Figure 11:
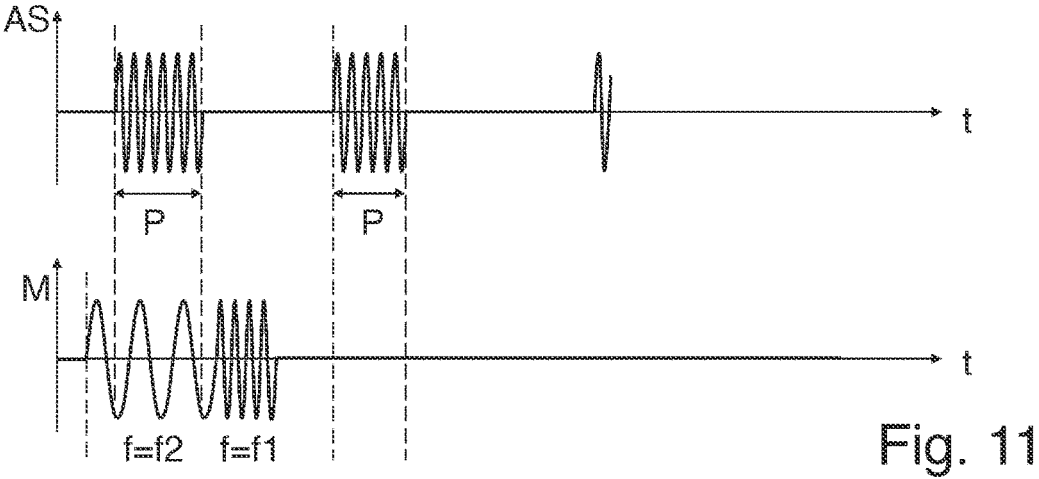

For determination of the at least one impedance absolute value and the at least one phase value, measurement signal M is applied to the electrode current circuit and thus the neutral electrode 23. As explained, the alternating measurement signal M can be an impressed alternating measurement voltage UM or an impressed alternating measurement current IM. The measurement signal M is at least applied to the neutral electrode 23 at two different measurement frequencies f, according to the example at a first measurement frequency f1 and a second measurement frequency f2 (FIGS. 9-11). Thereby the sequence of the set measurement frequencies f1, f2 can be selected arbitrarily. In the schematically time-dependent progresses of measurement signal M illustrated in FIGS. 9 to 11 only by way of example the second measurement frequency f2 is set first and the first measurement frequency f1 is set subsequently respectively.

In the examples illustrated in FIGS. 9 and 10 measurement signal M is respectively applied to the neutral electrode 23 outside the treatment periods P. In doing so, it is avoided that the working signal AS and the measurement signal M affect one another, because working signal AS also produces a current back flow to the supply apparatus 16 via neutral electrode 23.

Alternatively, it is also possible to allow at least temporarily an overlapping of measurement signal M and a treatment period P. In this case the measurement frequency f set during a treatment period P is clearly differently selected from the working frequency of working signal AS (working voltage UA and/or working current IA). Such a temporal overlap is illustrated in FIG. 11 by way of example.

Measurement signal M can be switched between the different measurement frequencies f1, f2 substantially without interruptions (FIGS. 9 and 11). Alternatively to this, measurement signal M can also be interrupted by a pause (FIG. 10). In this example the measurement signal M is interrupted by one or alternatively also multiple treatment periods P and thus measurement signal M is applied to the neutral electrode 23 at the different measurement frequencies f1, f2 with temporal distance.

At each set measurement frequency an impedance absolute value $ZN_{abs}$ and/or a phase value $\varphi$ can be determined by evaluation of the alternating measurement voltage UM and the alternating measurement current IM in the measurement unit 33. Based on the at least one impedance absolute value $ZN_{abs}$ and the at least one phase value $\varphi$, a comparison with predefined comparison values for the different electrode types T1, T2, T3 can be carried out and therefrom the connected electrode type T1, T2, T3 can be determined or identified.

Figure 7:
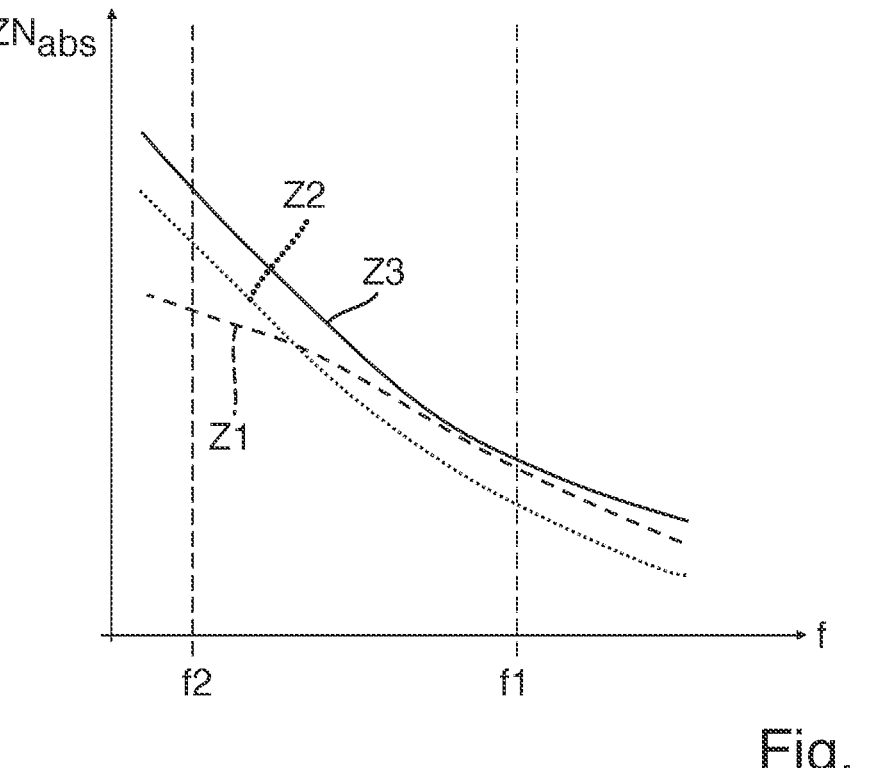
Figure 8:
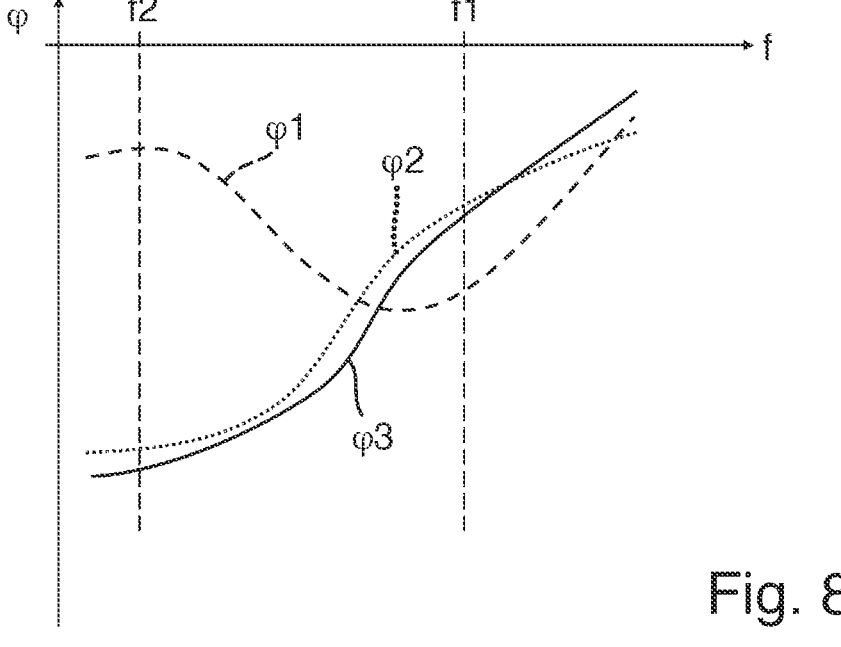

By way of example, comparison values in the form of comparison curves are illustrated schematically in FIGS. 7 to 8. A first impedance absolutes value curve Z1 describes the impedance absolute values $ZN_{abs}$ depending on the measurement frequency f for the first electrode type T1. Analog to this the second impedance absolute value curve Z2 describes the impedance absolute values $ZN_{abs}$ for the second electrode type T2 and the third impedance absolute value curve Z3 describes the impedance absolute values $ZN_{abs}$ for the third electrode type T3. A first phase curve $\varphi1$ describes phase values depending on the measurement frequency f for the first electrode type T1. Analog to this a second phase curve $\varphi2$ describes phase values $\varphi$ for the second electrode type T2 and a third phase curve $\varphi3$ describes phase values $\varphi$ for the third electrode type T3. The impedance absolute value curves Z1, Z2, Z3 are schematically illustrated in FIG. 7 and the phase curves $\varphi1$, $\varphi2$, $\varphi3$ are schematically and by way of example illustrated in FIG. 8. In addition, the measurement frequencies f1, f2 used, according to the example, are indicated in FIGS. 7 and 8.

As explained, it can be sufficient to determine the impedance absolute value $ZN_{abs}$ of the neutral electrode impedance ZN at the first measurement frequency f1 and the phase value $\varphi$ of neutral electrode impedance ZN at the second measurement frequency f2. Based on different frequency-dependent values for the impedance absolute value and the phase, the connected electrode type T1, T2, T3 can be recognized therefrom subsequently. At least for the used measurement frequencies f1, f2, the respectively assigned comparison values for the at least one impedance absolute value $ZN_{abs}$ and the at least one phase value $\varphi$ are pre-defined, e.g. in the measurement unit 33, so that the electrode type T1, T2, T3 can be recognized by comparison of the determined at least one impedance absolute value $ZN_{abs}$ and the determined at least one phase value $\varphi$.

It is again indicated that the impedance absolute values and the phase values can also be determined at more than one measurement frequency f respectively and the number of determined impedance absolute values and phase values can vary.

The invention refers to an electrosurgical system 15 as well as a method 50. The electrosurgical system 15 and the method 50 are configured to determine an electrode type T1, T2, T3 of a used neutral electrode 23. For this an alternating measurement signal M is applied to the neutral electrode 23 at least at two different measurement frequencies f1, f2. At each measurement frequency f1, f2 an impedance absolute value $ZN_{abs}$ or a phase value $\varphi$ or both is determined for the neutral electrode impedance ZN of neutral electrode 23. At least one impedance absolute value $ZN_{abs}$ and at least one phase value $\varphi$ are determined. Based on the at least one impedance absolute value $ZN_{abs}$ and the at least one phase value $\varphi$, the electrode type T1, T2, T3 of the connected neutral electrode 23 is determined—particularly by comparison with known comparison values for the at least one impedance absolute value $ZN_{abs}$ and the at least one phase value $\varphi$.

The invention claimed is:

1. A Method for determining an electrode type of a neutral electrode comprising the following steps:
   attaching the neutral electrode to a patient so that an electrically conductive connection exists between the neutral electrode and the patient,
   applying an alternating measurement signal at least at two different measurement frequencies to the neutral electrode respectively,
   determining at least one impedance absolute value of a neutral electrode impedance of the neutral electrode for at least one of the at least two different measurement frequencies,
   determining at least one phase value of the neutral electrode impedance of the neutral electrode for at least one of the at least two different measurement frequencies,
   determining an electrode type of the connected neutral electrode based on the at least one impedance absolute value and the at least one phase value; and,
   setting at least one of an electric power limit, a current limit, and/or an operating mode of an electrosurgical system based on the determined electrode type.

2. The method of claim 1, further comprising determining an impedance absolute value ($ZN_{abs}$) of the neutral electrode impedance (ZN) for a first measurement frequency of the at least at two different measurement frequencies and a phase value of the neutral electrode impedance for a second measurement frequency of the at least at two different measurement frequencies, wherein the second measurement frequency is smaller than the first measurement frequency.

3. The method according to claim 2, wherein the first measurement frequency is in the range of 5.0 kHz to 1.0 MHz.

4. The method according to claim 2, wherein the second measurement frequency in the range of 100 Hz to 5.0 kHz.

5. The method according to claim 1, wherein the neutral electrode comprises an electrically conductive first electrode section and an electrically conductive second electrode section, and wherein the electrical potentials of which are separated from one another.

6. The method according to claim 5, wherein the first electrode section and the second electrode section are arranged symmetrically with regard to a reference plane.

7. The method according to claim 5, wherein the neutral electrode comprises an electrically conductive third electrode section, and wherein the electrical potential of which is separated from the electrical potentials of the first electrode section and the second electrode section.

8. The method according to claim 7, wherein the third electrode section surrounds the first electrode section and the second electrode section.

9. The method according to claim 5, wherein on sides facing away from one another the first electrode section and the second electrode section comprise outer edges curved in an arc-shaped manner.

10. The method according to claim 5, wherein on sides facing away from one another the first electrode section and the second electrode section comprise an outer edge, which is substantially straight.

11. An Electrosurgical system adapted for use with the method of claim 1, the system comprising:
   a supply apparatus coupled to the neutral electrode by a neutral connection; and
   a measurement unit, the measurement unit comprising:
      a signal generator configured to apply the alternating measurement signal; and,
      at least one of a current sensor and a voltage sensor, the measurement unit configured to execute the determining at least one impedance absolute value step, the determining at least one phase value step, and the determining an electrode type step.

12. The electrosurgical system according to claim 11, wherein the supply apparatus comprises a supply connection and an instrument having a working electrode electrically connected to the supply connection, wherein the supply apparatus and/or the instrument is configured to provide a working voltage and/or a working current (IA) for the working electrode.

13. The electrosurgical system according to claim 12, wherein the supply apparatus is configured to apply a measurement signal only to the neutral connection, if no working voltage and no working current is supplied to the working electrode.

14. The electrosurgical system according to claim 12, wherein the supply apparatus is configured to select a measurement frequency of the alternating measurement signal different from a working frequency of a working voltage or working current (IA), if the alternating measurement signal is applied to the neutral connection while a working voltage or a working current is supplied to the working electrode.

15. The electrosurgical system according to claim 11, further comprising a plurality of predefined operating modes, and the supply apparatus is configured to select the operating mode dependent on the determined electrode type, wherein the operating mode is adapted to the electrode type, which can be set manually or automatically.

\* \* \* \* \*